(12) United States Patent
Goss

(10) Patent No.: US 11,154,291 B2
(45) Date of Patent: Oct. 26, 2021

(54) SURGICAL MEDICAL SUTURE NEEDLE WITH SURGICAL SUTURE AND ANCHOR SYSTEM

(71) Applicant: KARL STORZ GmbH & Co. KG, Tuttlingen (DE)

(72) Inventor: John Goss, Sutton, MA (US)

(73) Assignee: KARL STORZ SE & Co. KG, Tuttlingen (DE)

( * ) Notice: Subject to any disclaimer, the term of this patent is extended or adjusted under 35 U.S.C. 154(b) by 156 days.

(21) Appl. No.: 15/668,062

(22) Filed: Aug. 3, 2017

(65) Prior Publication Data

US 2018/0035996 A1 Feb. 8, 2018

Related U.S. Application Data

(60) Provisional application No. 62/370,446, filed on Aug. 3, 2016.

(51) Int. Cl.
*A61B 17/04* (2006.01)
*A61B 17/42* (2006.01)
*A61B 17/02* (2006.01)
*A61B 17/06* (2006.01)

(52) U.S. Cl.
CPC ...... *A61B 17/0401* (2013.01); *A61B 17/0218* (2013.01); *A61B 17/42* (2013.01); *A61B 17/06066* (2013.01); *A61B 2017/042* (2013.01); *A61B 2017/0404* (2013.01); *A61B 2017/0417* (2013.01); *A61B 2017/0464* (2013.01);
(Continued)

(58) Field of Classification Search
CPC .......... A61B 17/0401; A61B 17/06166; A61B 17/0218; A61B 17/04; A61B 17/06; A61B 17/0644; A61B 17/083; A61B 17/10; A61B 17/11; A61B 17/12009; A61B 17/42; A61B 2017/0417; A61B 2017/0409; A61B 2017/0464; A61B 2017/06057; A61B 2017/0459; A61B 2017/0412; A61B 2017/0427; A61B 2017/06052; A61B 2017/00477; A61B 2017/00805
See application file for complete search history.

(56) References Cited

U.S. PATENT DOCUMENTS 4,235,238 A 11/1980 Ogiu et al.
4,705,040 A 11/1987 Mueller et al.
(Continued)

FOREIGN PATENT DOCUMENTS

DE 695 32 952 T2 1/2005
DE 601 22 756 T2 9/2007
(Continued)

*Primary Examiner* — Mohamed G Gabr
(74) *Attorney, Agent, or Firm* — Muncy, Geissler, Olds & Lowe, P.C.

(57) ABSTRACT

A cervical retraction system includes a suture having a first end and a second end, a cervical anchor secured to the first end of the suture and a curved needle secured to the second end of the suture. A method of retracting a cervix includes providing the cervical retraction system, inserting the curved needle through tissue of a cervix of a patient, advancing the needle along a trajectory of a curve of the needle until it emerges through an external os of the cervix and applying counter tension by pulling the needle out through the external os.

15 Claims, 10 Drawing Sheets

(52) U.S. Cl.
CPC .......... *A61B 2017/0496* (2013.01); *A61B 2017/0608* (2013.01); *A61B 2017/4225* (2013.01)

(56) References Cited

U.S. PATENT DOCUMENTS

| | | | |
|---|---|---|---|
| 5,362,294 A * | 11/1994 | Seitzinger | A61B 17/0218 600/37 |
| 5,954,057 A | 9/1999 | Li | |
| 6,610,071 B1 * | 8/2003 | Cohn | A61B 17/06166 606/148 |
| 8,696,704 B2 | 4/2014 | Selvitelli et al. | |
| 2004/0116963 A1 * | 6/2004 | Lattouf | A61B 17/0401 606/224 |
| 2005/0187577 A1 | 8/2005 | Selvitelli et al. | |
| 2005/0267531 A1 * | 12/2005 | Ruff | A61B 17/04 606/228 |
| 2006/0030884 A1 | 2/2006 | Yeung et al. | |
| 2010/0305566 A1 | 12/2010 | Rosenblatt et al. | |
| 2013/0066423 A1 * | 3/2013 | Bishop | A61B 17/06166 623/8 |

FOREIGN PATENT DOCUMENTS

| | | |
|---|---|---|
| DE | 603 15 694 T2 | 6/2008 |
| DE | 60 2005 002 853 T2 | 7/2008 |
| DE | 10 2008 045 877 A1 | 3/2010 |
| DE | 11 2011 102 552 T5 | 5/2013 |
| EP | 1 013 229 B1 | 12/1999 |
| EP | 2 543 341 B1 | 6/2005 |
| EP | 2 237 727 B1 | 1/2009 |
| EP | 2 308 383 B1 | 8/2010 |
| WO | WO 03/077772 A1 | 12/2002 |

* cited by examiner

SURGICAL MEDICAL SUTURE NEEDLE WITH SURGICAL SUTURE AND ANCHOR SYSTEM

This nonprovisional application claims priority to U.S. Provisional Application No. 62/370,446, which was filed on Aug. 3, 2016, and which is herein incorporated by reference.

BACKGROUND OF THE INVENTION

Field of the Invention

The present invention relates to a surgical suture device, in particular, a method and retraction system that assists in manipulating and suspending a patient's cervix at a desired position during diagnostic and surgical procedures.

Description of the Background Art

There are numerous conventional gynecologic instruments used during diagnostic and surgical procedures. For example, uterine manipulators are used during gynecologic laparoscopy procedures to facilitate visualization of pelvic organs. Hysteroscopes are used in transvaginal ultrasound procedures. Cervical dilators are used in gynecologic procedures in which the cervix must be open, allowing access to the uterus and fallopian tubes. The dilator is used to open the cervix in less time in preparation for a surgical procedure. Resectoscopes are used to extract tissue for a biopsy or remove growths from, for example, a patient's uterus. Ablation devices are commonly used to remove diseased or damaged tissue. Also, hysteroscopic morcellators are used to remove polyps or submucous myomas. For example, U.S. Patent Application Publication No. 2010/0305566 discloses a hysterectomy method that includes severing a patient's uterus from the patient's cervix, coring the cervix and then morcellating the severed uterus using a morcellator inserted through the cored cervix.

With each of the above procedures, it is necessary to stabilize a patient's cervix. Currently, tenaculum forceps are used to grab, hold and stabilize a patient's cervix while a medical procedure, such as those described above, for example, is being performed. Tenaculum forceps are a type of locking forceps, which include a slender sharp-pointed hook attached to a handle, and which holds itself in place in the position in which it has been locked. Tenaculum forceps allow the cervix to be held and retracted in a steady manner while the surgical procedure is conducted. Tenaculum forceps for gynecologic procedures may be manufactured using plastic or steel. Steel forceps can be sterilized and, thus, can be re-used where forceps made from plastic are only intended to be used once on a single patient. The plastic forceps are generally disposed of after a single use.

Anesthesia is generally provided to the patient who is undergoing a procedure that makes use of the tenaculum forceps. There are times when the patient may be left to remain awake but a local anesthesia is provided so that the insertion and the removal of the gynecologic instrument are not felt. Along with anesthesia, medication is also provided to the patient so that the patient can remain relaxed through the procedure. It is quite common, however, that patients may feel the instruments that surgeons/doctors use on them, but using the correct type of forceps can help make sure the procedure is conducted smoothly and without any discomfort. If the incorrect instruments are used, then tissue can be severely damaged, which can further cause infection and increase healing time.

There are, however, several disadvantages to using the tenaculum forceps. First, tenaculum forceps use a lot of space when deployed and applied in the area of operation. Second, tenaculum forceps are expensive to manufacture. Third, while tenaculum forceps, made from steel, can be sterilized after use, a proper sterilization process involves proper performance of several steps in series. The sterilization process is labor intensive, expensive and time consuming.

Moreover, sutures and suture/bone anchors are used for repairing tissue in surgical procedures to secure soft tissue to bone. Specifically, tears in soft tissues such as cartilage, ligament or muscle can be repaired by suturing. Suture anchors are commonly used during the surgical procedure to provide an attachment location for the suture. The suture anchor may be secured into a bone by inserting the anchor into a pre-formed hole in the bone.

For example, U.S. Pat. No. 4,235,238 discloses a coeliac tissue-suturing apparatus including a flexible tubular member, inserted into an endoscope, and a needle. The device is configured to set suture threads on tissues around a coeliac bleeding spot.

Furthermore, DE 10 2008 045 877 discloses a device for fixing tissue. The device includes a handle at one end of a tubular member and an anchor at another end of the tubular member. A suture is secured to the anchor. The device also includes a suction member configured to hold the tissue in place while the suture is set.

In another example, U.S. Patent Application Publication No. 2006/0030884 (and similarly WO 03/077772) discloses an elastically curved suture anchor that is delivered into tissue by a needle. A fin protrudes from one side of the anchor and a platform covers the opposite side of the anchor. The fin is on the concave side and the platform is on the convex side. A suture passes through an opening in the platform, loops around the concave side of the anchor and passes through another opening in the platform. As a result, both strands of the suture can be pulled from the convex side of the anchor.

U.S. Pat. No. 8,696,704 (and similarly DE 20 2005 002 853 and U.S. Patent Application Publication No. 2005/0187577) discloses suture anchor systems for repairing torn or damaged tissue. The system includes a first suture loop having a first suture anchor couple thereto. A slip knot is formed thereon to allow a size of the first loop to be adjusted. A second suture loop, having a second suture anchor, is coupled to the first suture loop. The suture anchors can be deployed through tissue to be repaired and into the anchoring tissue at a position spaced apart from one another. The length of the first loop can be tensioned to re-approximate the torn or damaged tissue toward the anchoring tissue.

Additional sutures and/or suture anchor devices are disclosed in EP 1 013 229, EP 2 543 341, DE 603 15 694, DE 11 2011 102 552, DE 601 22 756 and DE 695 32 952.

Other conventional devices have been developed for retracting and/or holding tissue during surgical procedures. For example, U.S. Pat. No. 4,705,040 discloses a device for percutaneous fixation of a hollow organ. The device includes a needle carrying a retaining device that is attached to a tension filament. The retaining device is inserted into the skin and the retaining device is released from the needle. The organ is fixed by adjusting tension on the filament and clamping the filament outside the body.

U.S. Pat. No. 5,954,057 discloses a suspension clip assembly for suspending soft tissue from a bodily support structure. The suspension clip assembly includes a suspension clip having a point for penetrating soft tissue. A suspension strap is mounted to an end of the clip and is adapted so that a proximal end of the strap can be attached to the bodily support structure.

EP 2 308 383 discloses a system for retracting tissue during a surgical procedure. The system includes an anchor, an anchoring component attached to a base of the anchor and a cam cleat attached to another end of the base. The system also includes a suture having an attachment device secured to an end of the suture. The suture is operable to suspend tissue and/or organs from an abdominal wall by pulling the suture through the cam cleat.

EP 2 237 727 discloses a tissue retractor. The retractor includes a base that is configured to be attached to a surface adjacent to an incision and a retractable member adapted to receive a tissue hook. The hook is configured to engage tissue to be retracted. The retractable member is retractable away from the incision to retract tissue away from the incision.

These documents, however, do not overcome all of the disadvantages of the tenaculum forceps. Thus, there remains a desire to obtain a minimally invasive, yet highly effective, alternative to the standard technique that can be used to stabilize a patient's cervix while the cervix is manipulated during a gynecologic surgical procedure.

SUMMARY OF THE INVENTION

In view of the foregoing and other exemplary problems, drawbacks, and disadvantages of the conventional methods and compositions, an exemplary feature of the present invention is to provide an economical needle-thread-anchor system that is delivered as one retraction unit in order to stabilize a patient's cervix while the cervix is manipulated during a gynecologic surgical procedure.

In accordance with an exemplary embodiment of the present invention, a cervical retraction system includes a suture having a first end and a second end, a cervical anchor secured to the first end of the suture thread and a curved needle secured to the second end of the suture.

In accordance with an exemplary embodiment of the present invention, a method of retracting a cervix includes providing a cervical retraction system, the cervical retraction system including a suture having a first end and a second end, a cervical anchor secured to the first end of the suture and a curved needle secured to the second end of the suture, inserting the curved needle through tissue of a cervix of a patient, advancing the needle along a trajectory of a curve of the needle until it emerges through an external opening (i.e., os) of the cervix and applying counter tension by pulling the needle out through the external os.

In accordance with an exemplary embodiment of the present invention, a cervical retraction system, includes a cervical anchor having a first end and a second end, a first suture secured to and extending from the first end, a second suture secured to and extending from the second end, a first curved needle secured to an end of the first suture and a second curved needle secured to an end of the second suture.

Thus, the present invention provides a needle-thread-anchor system that is easily secured to a patients' cervix to provide sufficient counter traction to stabilize the patients' cervix during a surgical procedure that is both economical and minimally invasive.

Moreover, the present invention provides a needle-thread-anchor system that can be manufactured and preassembled in an easy and cost-effective manner, and which can be provided and encased under a sterile condition in, for example, a blister package.

Still further, the operation of the needle-thread-anchor system of the present invention may be easily and quickly learned so that a user can quickly apply the needle-thread-anchor system after a short practice period. Thus, the needle-thread-anchor system of the present invention offers the advantage that a suture operation is unfailingly carried out.

Additionally, with the needle-thread-anchor system of the present invention, since the individual components are interconnected and the system consists of the individual components intended to contribute together to a clearly defined function, the needle-thread-anchor system of the present invention can be quickly and flexibly adjusted to a desired application site on the patient's cervix.

Moreover, in use, the needle-thread-anchor system of the present invention can be deployed quickly and, due to the small size of the individual components, the needle-thread-anchor system of the present invention saves space, which offers a medical professional improved visibility on the application site and also allows additional space for other instruments used in the medical procedure.

Further scope of applicability of the present invention will become apparent from the detailed description given hereinafter. However, it should be understood that the detailed description and specific examples, while indicating preferred embodiments of the invention, are given by way of illustration only, since various changes, combinations, and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, do not limit the present invention, and wherein.

DETAILED DESCRIPTION

Certain exemplary embodiments and aspects of the present invention are directed to a method of deploying, setting and securing of cervix anchors to a wall of a cervix and urging the anchor against the cervix so as to displace and/or retract the cervix in a longitudinal direction during gynecologic procedures. Additionally, certain exemplary embodiments and aspects of the present invention are directed to a cervical retraction system for use in the above method. Each particular anchor is adapted for attachment to the cervix within a patient's vagina such that attachment to the cervix allows for selective placement of the individual anchor to support the retraction of the cervix.

Figure 1:
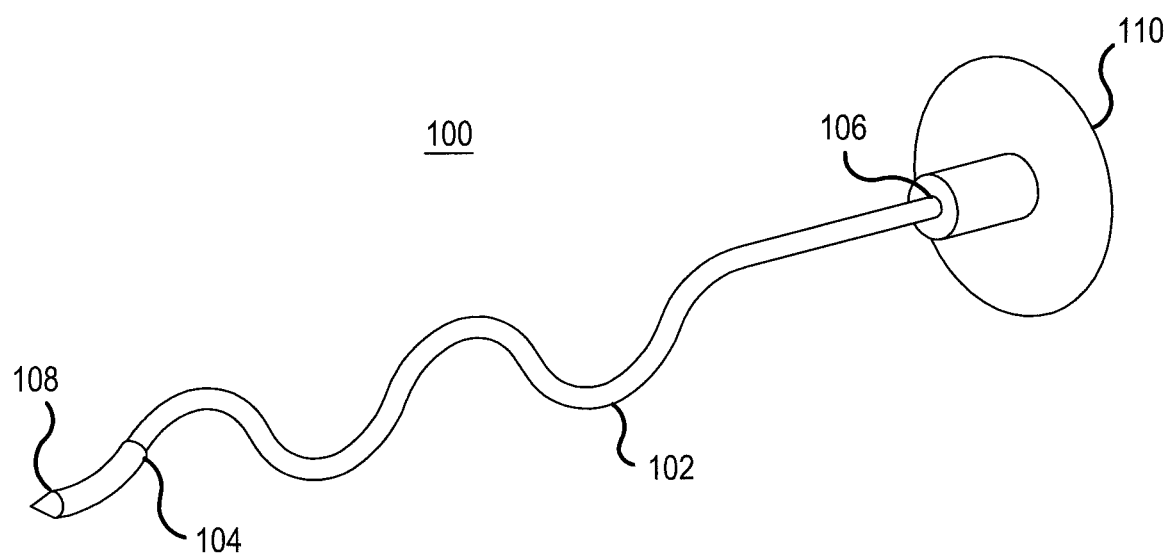
FIG. 1 illustrates a cervical retraction system 100 according to an exemplary embodiment of the present invention.

FIG. 1 illustrates a cervical retraction system 100 according to a first, exemplary embodiment of the present invention. In accordance with the embodiment illustrated in FIG. 1, the cervical retraction system 100 includes a suture 102 having a first end 104 and a second end 106. A curved needle 108 is secured to the first end 104. The suture 102 may be fixed to the curved needle 108 or threaded through an eye of the needle 108. The suture 102 is then swagged onto the needle 108. A suture anchor 110 is firmly secured to the second end 106 of the suture 102.

For example, the anchor 110 may be crocheted or knit from monofilament the thread. That is, the suture anchor can be a respective/individual woven/braided part or portion of the monofilament thread. Thus, with regard to the embodiment illustrated in FIG. 1, the anchor 110 is knitted to finally adopt the shape/design of a thumb tack. A further possibility to use the thread in a particular way is to ensnare a specifically-shaped anchor as to finally provide a needle-thread-anchor system with no particular or physical configuration at the transition/connecting point.

The suture anchor 110 can be made of biocompatible material such as stainless steel, titanium, a titanium alloy, peek, polyethylene or carbon. With regards to the aforementioned material, the suture material can operatively be connected to the anchor in different ways, which depend on the form and function of the anchor to be placed. If the material is, for example, stainless steel, the thread can be swaged onto a side of the anchor. Moreover, the suture anchor 110 can be designed to provide a slit and/or eyelet through which the thread can be passed through.

Figure 2:
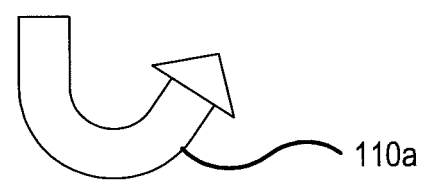
FIG. 2 illustrates an embodiment of an anchor of the cervical retraction system 100.
Figure 3:
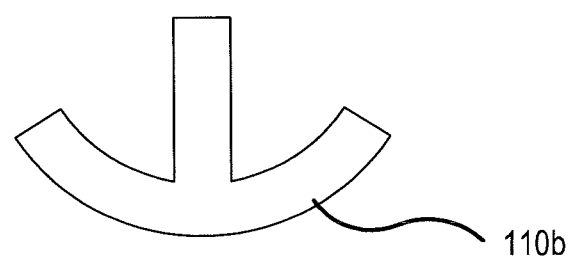
FIG. 3 illustrates an embodiment of an anchor of the cervical retraction system 100.

The design of the anchor 110 can take several shapes and can be optimized and adapted to the shape and size of an individual patient's cervix. For example, in the embodiment illustrated in FIG. 1, the anchor 110 has a thumb-tack shape design. In the embodiment illustrated in FIG. 2, the anchor 110a has a hook shape. In the embodiment illustrated in FIG. 3, the anchor 110b has a T-bar shape. The shapes of the anchors 110/110a/110b illustrated in FIGS. 1-3 are non-limiting examples of the potential anchor designs.

Figure 4:
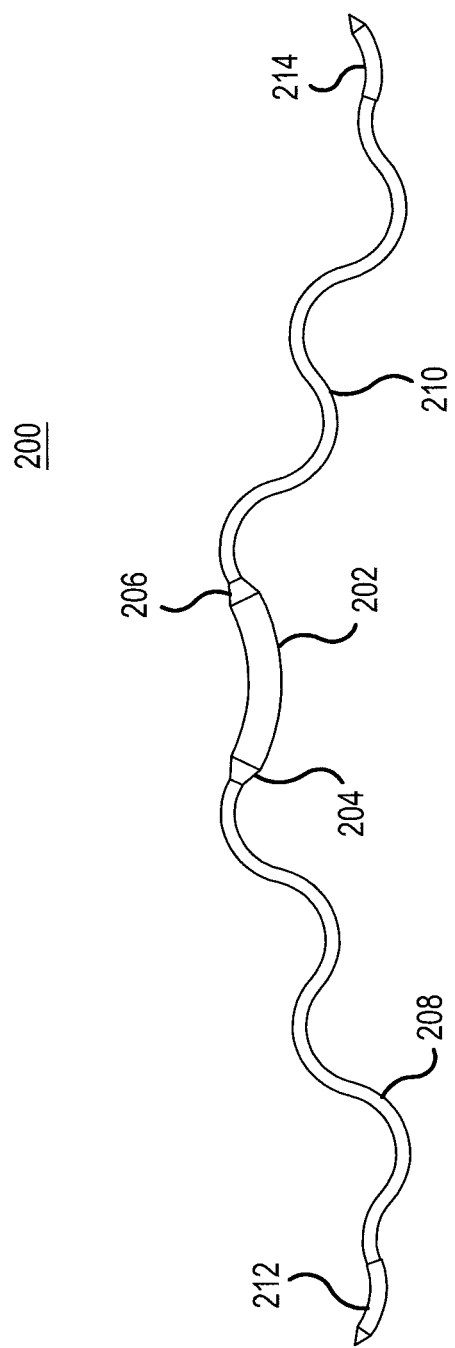
FIG. 4 illustrate a cervical retraction system 200 according to an exemplary embodiment of the present invention.

FIG. 4 illustrates a cervical retraction system 200 according to a second, exemplary embodiment of the present invention. In the embodiment illustrated in FIG. 4, the cervical retraction system 200 includes a quadrangular, plate-shaped anchor 202. The anchor 202 is slightly bent with respect to its longitudinal axis. The anchor 202 has a first end 204 and a second end 206 opposite to the first end 204. A first suture 208 is secured to the first end 204 of the anchor 202 and a second suture 210 is secured to the second end 206 of the anchor 202. The sutures 208/210 are firmly and operatively attached to the respective ends 204/206 of the anchor 202. For example, the sutures 208/210 may be secured to the anchor 202 through mounting holes or eyelets. The mounting holes or eyelets are located transverse to the longitudinal axis of the anchor body. The cervical retraction system 200 also includes a first curved needle 212 secured to the first suture 208 and a second curved needle secured to the second suture 210. The sutures 208/210 may be fixed to the curved needles 212/214 or threaded through an eye of the needles 212/214. Thus, the cervical retraction system 200 provides a symmetrical assembly.

Similar to that discussed above with respect to the embodiment illustrated in FIG. 1, the sutures 208/210 can be kitted to the anchor 202. If the anchor has been designed and configured to provide and define a lumen, the resilient band can be positioned within the lumen so as to enable the doctor to re-place and position the anchor on the band/tape relative to the stich points.

In accordance with the cervical retraction system 100 or the cervical retraction system 200, the sutures can be designed as a resilient band/strap. This design is advantageous and beneficial in comparatively soft cervix tissue and minimizes the risk of causing excessive stress for fissuring of the tissue around the puncture site.

For each of the anchor designs illustrated in FIGS. 1-4, the respective shape ensures that no pull out of the anchors is possible. The anchor defines a lumen and the suture can be positioned within the lumen so to enable a doctor to replace the anchor on the suture relative to the insertion point of the needle.

Figure 5A:
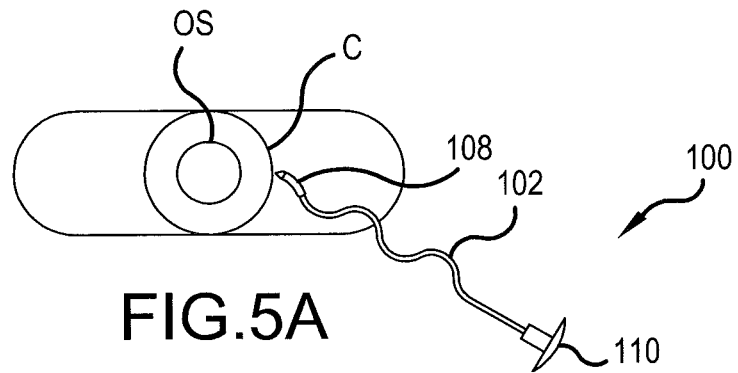
FIGS. 5A-5C illustrate a method of placement of the cervical retraction system 100.
Figure 5B:
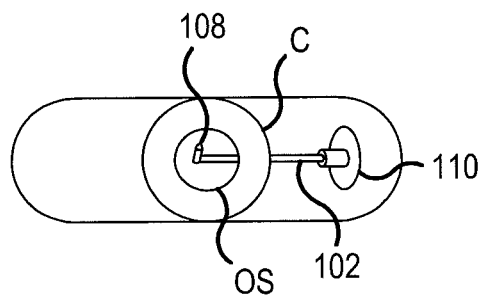
Figure 5C:
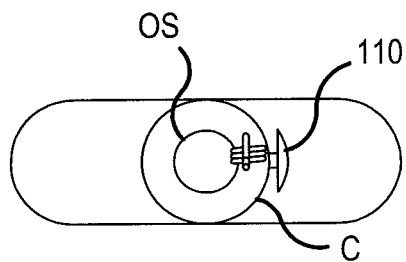

FIGS. 5A-5C illustrate a method of placement of the cervical retraction system 100. As illustrated in FIG. 5A, the cervical retraction system 100 is placed by mounting the curved needle into a needle holder.

Figure 8:
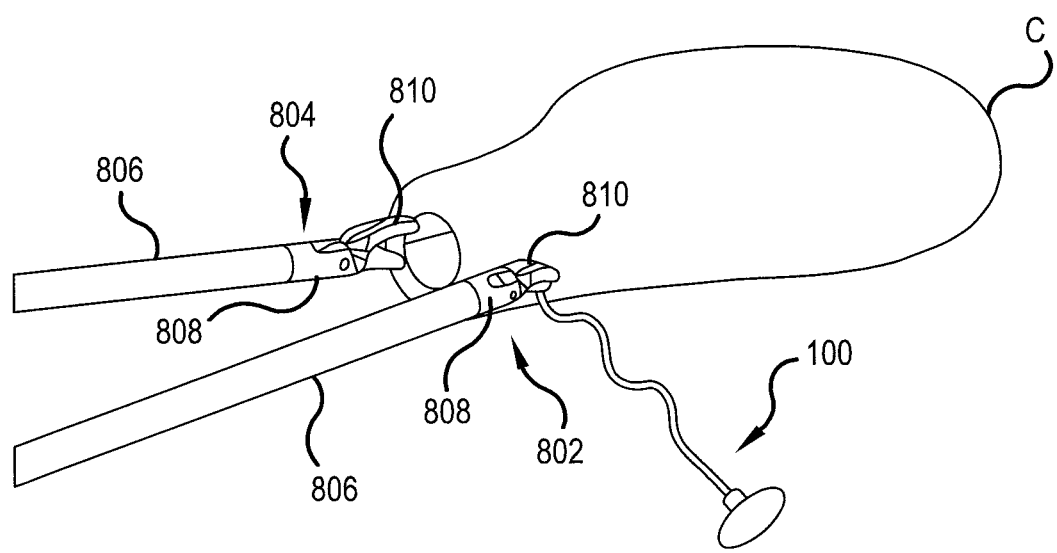
FIG. 8 illustrates a needle holder, used in placement of the cervical retraction system, in accordance with certain exemplary embodiments of the invention.

A needle holder arrangement is illustrated in FIG. 8. The system of the present invention can use one or two needle holders. The embodiment illustrated in FIG. 8 illustrates a first needle holder 802 and a second needle holder 804. The needle holders are configured to hold the needle of the curved needle 108/212/214. Each needle holder 802/804 includes a shaft portion 806, a joint 808 formed at an end of the shaft portion 806 and a pair of movable jaws 810 disposed on the joint 808. To maintain a firm grip on the needle, the jaws 810 may be textured. Additionally, the jaws 810 may be short as compared to the shaft portion 806 to increase the applied force, similar to the principals of a lever. As is illustrated in FIG. 8, the first needle holder 802 is firmly holding the needle 108 of the cervical retraction system 100 while the needle is being inserted into the cervix C. The second needle holder 804 is positioned in front of the cervix os (OS) to grasp the needle 108 when it delivered through the tissue of the cervix C so that the user can pull the suture 102 and deploy the anchor 110.

Figure 9:
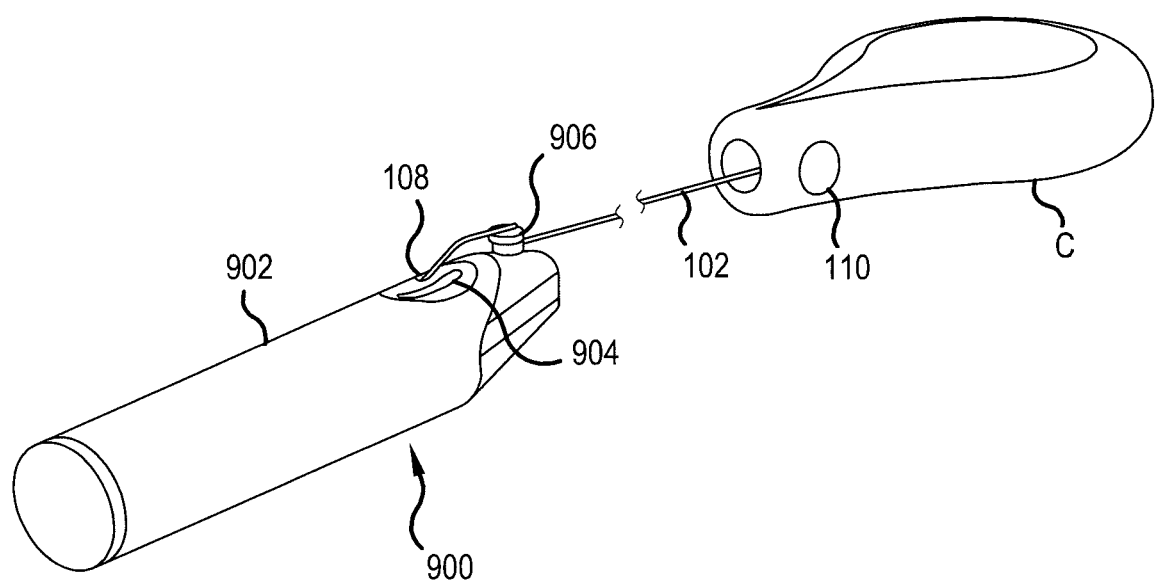
FIG. 9 illustrates a thread holder device 900.

FIG. 9 illustrates a thread holder that may be used in conjunction with the needle holder arrangement illustrated in FIG. 8. Specifically, FIG. 9 illustrates a thread holder device 900. The thread holder device 900 is used to exert a one-sided pull on the cervical retraction system 100/200. Conventionally, a user could hold and pull the suture thread by hand while the medical procedure is completed. Since the needle is still attached to the thread, a user is subject to potential cuts from the needle or is required to cut the needle off from the suture after the suture is deployed. The thread holder device 900 allows a user to safely secure the suture thread during the remaining surgical procedure.

The device 900 has a cylindrical main body 902 forming a hand grip. A needle receiving slot 904 is formed on a top of the main body 902. A suture winding member 906 is disposed at an end of the main body 902. The suture winding member 906 can include a spool or fastening pin/bar element configured to receive the suture 102. The suture winding member 906 is arranged at a distal end of the hand grip to firmly wind the suture thread(s) in such a way that the suture thread will not slide away when the user is holding the hand grip 902 and exerting a one-sided pull. Once the cervical retraction system 100 is deployed in the cervix C, the user may tightly wind the suture 102 around suture winding member 906 to firmly wrap the suture 102 in place.

The needle 108 is then placed into the slot 904. Thus, the cervical retraction system 100 can then be held firmly in place while any remaining surgical procedure is conducted. Thus, the first needle holder 802 and the second needle holder 804 are used when inserting and deploying the cervical retraction system 100/200. The thread holder device 900 is then used to hold and maintain the cervical retraction system 100/200 after it has been deployed.

A point of the needle 108 is pressed into and delivered through tissue of a patient's cervix C. As is illustrated in FIG. 5B, the needle 108 is advanced through the tissue of the cervix C along a trajectory of the curvature of the curved needle 108 until the needle 108 emerges from and is pulled through the external os (OS) of the cervix C. The cervix C has an ectocervix, which is a passage between the uterus and the vagina. The external os (OS) is an opening in a center of the ectocervix. As is illustrated in FIG. 5C, the needle 108 is pulled until the anchor 110 is secured against an outer wall of the cervix C at the initial insertion point of the needle 108. In order to generate the required retraction force on the cervix C, the surgeon must exert and apply a one-sided pull/force on the suture 102 by holding the suture 102 in his hands.

Figure 6A:
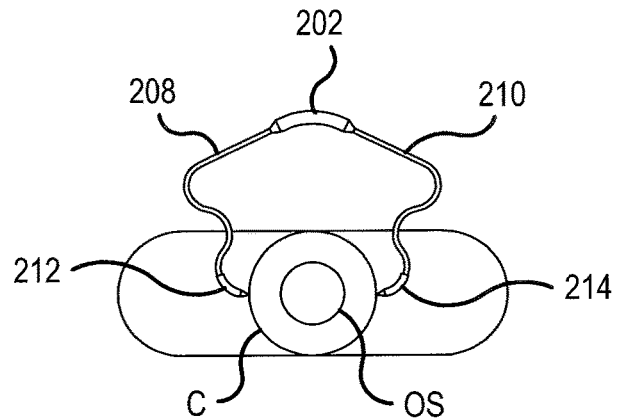
FIGS. 6A-6C illustrate a method of placement of the cervical retraction system 200.
Figure 6B:
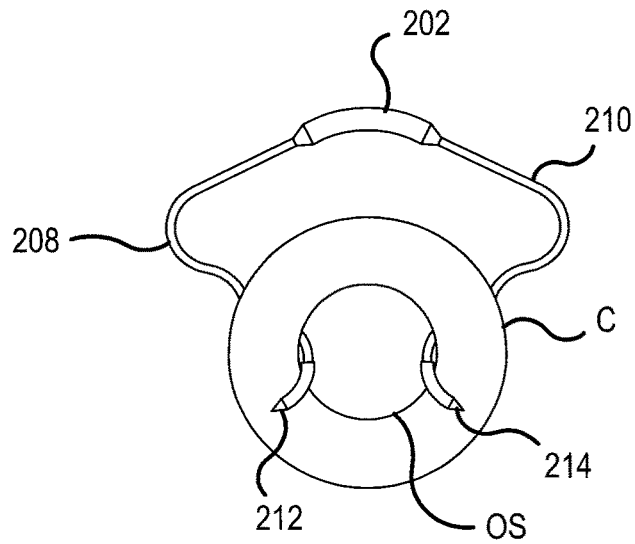
Figure 6C:
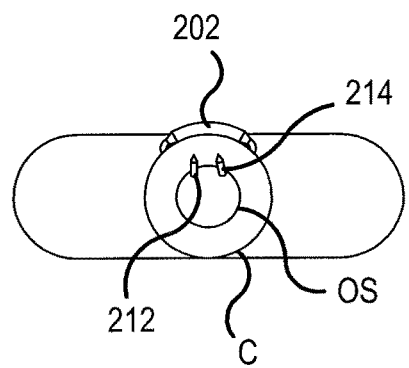
Figure 7A:
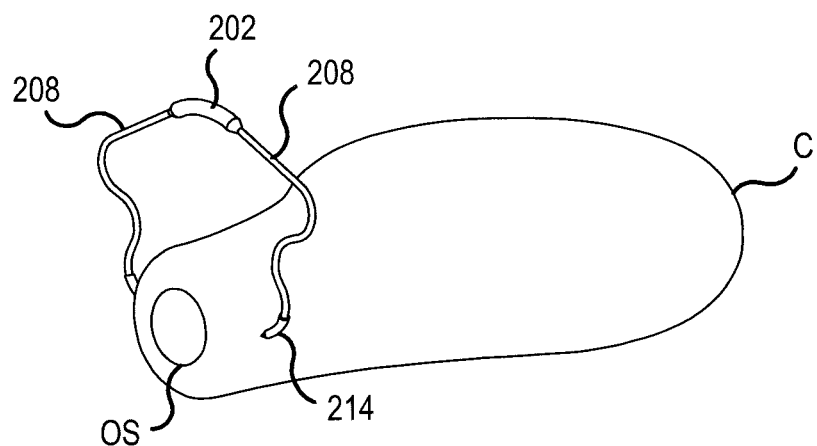
FIGS. 7A and 7B illustrate perspective views of the method illustrated in FIG. 6A-6C.
Figure 7B:
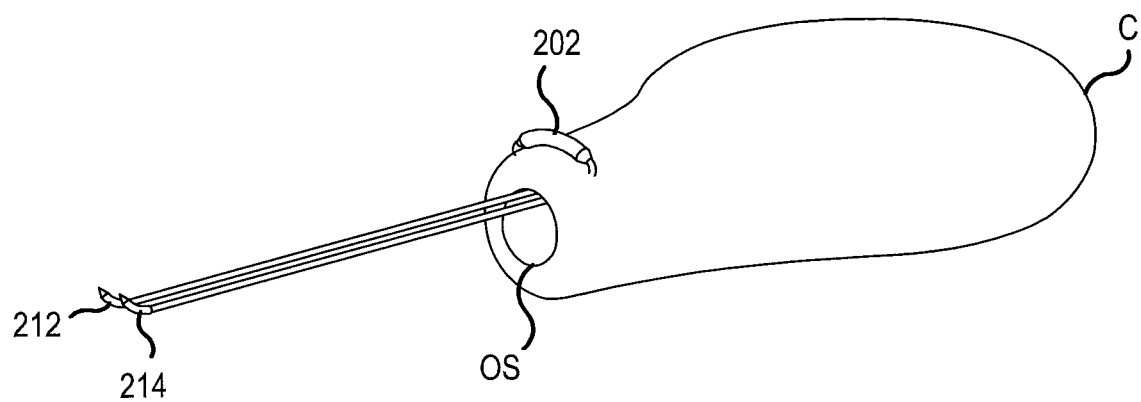

FIGS. 6A-6C illustrate a method of placement of the cervical retraction system 200. As illustrated in FIG. 6A, a point of each of the needles 212/214 is pressed into and delivered through tissue of a patient's cervix C. As is illustrated in FIG. 6B, the needles 212/214 are advanced through the tissue of the cervix C along a trajectory of the curvature of the curved needles 212/214 until the needles 212/214 emerge from and are pulled through the external os (OS) of the cervix C. As is illustrated in FIG. 6C, the needles 212/214 are pulled until the anchor 202 is secured against an outer wall of the cervix C at the initial insertion point of the needles 212/214. In order to generate the required retraction force on the cervix C, the surgeon must exert and apply a one-sided pull/force on the sutures 208/210 by holding the sutures 208/210 in his hands.

Once either of the cervical retraction system 100 or the cervical retraction system 200 is properly mounted, the surgeon may apply counter tension against the cervix C by pulling the sutures to allow the surgeon to insert another medical device into the external opening (OS) of the cervix C during a gynecological procedure.

In accordance with the cervical retraction system 100 or the cervical retraction system 200, cervical retraction system is removed using forceps to grasp the anchor and to pull the anchor out together with the suture and needles.

Figure 10:
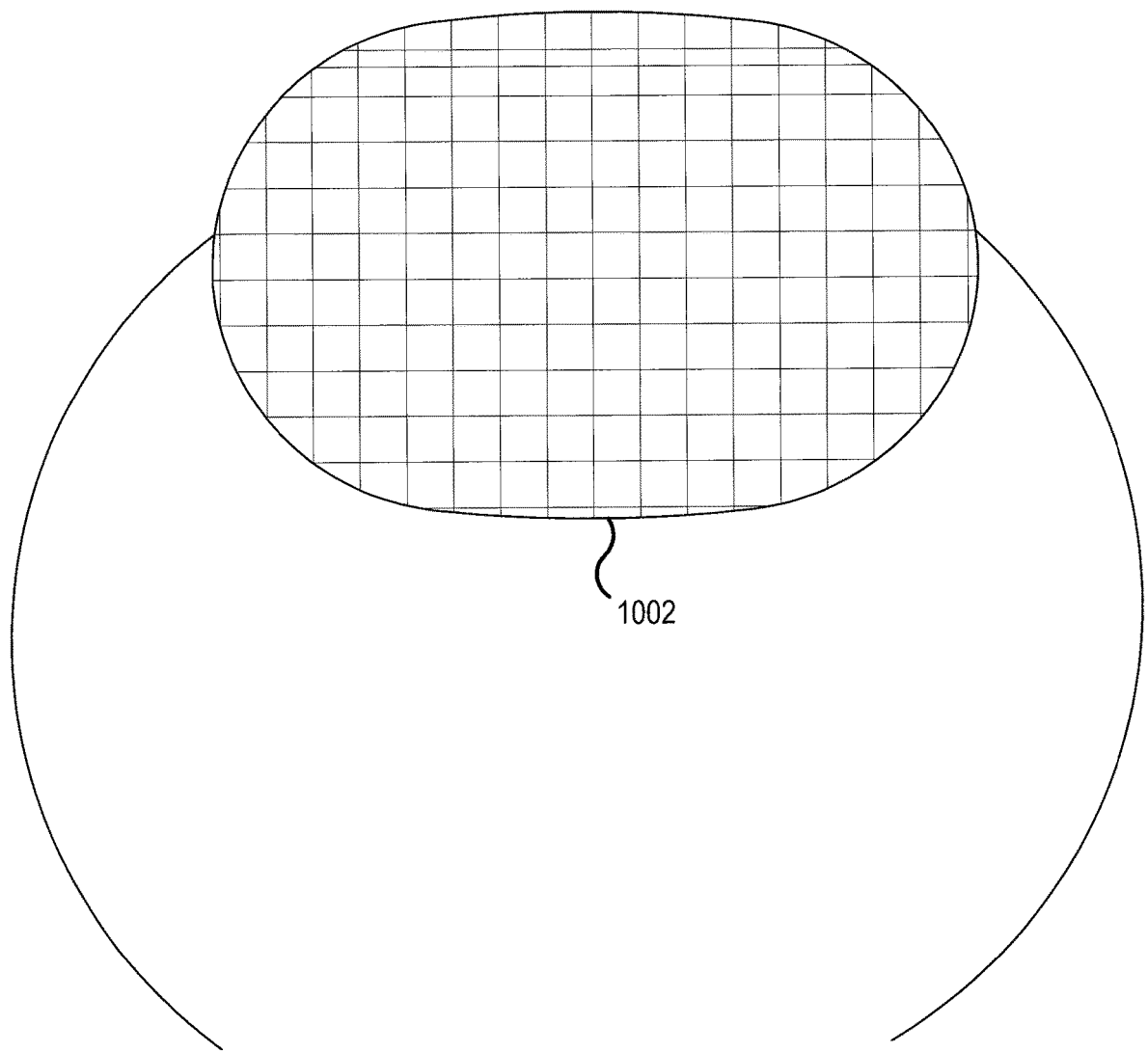
FIG. 10 illustrates an alternative embodiment of an anchor of the cervical retraction system 100.
Figure 11:
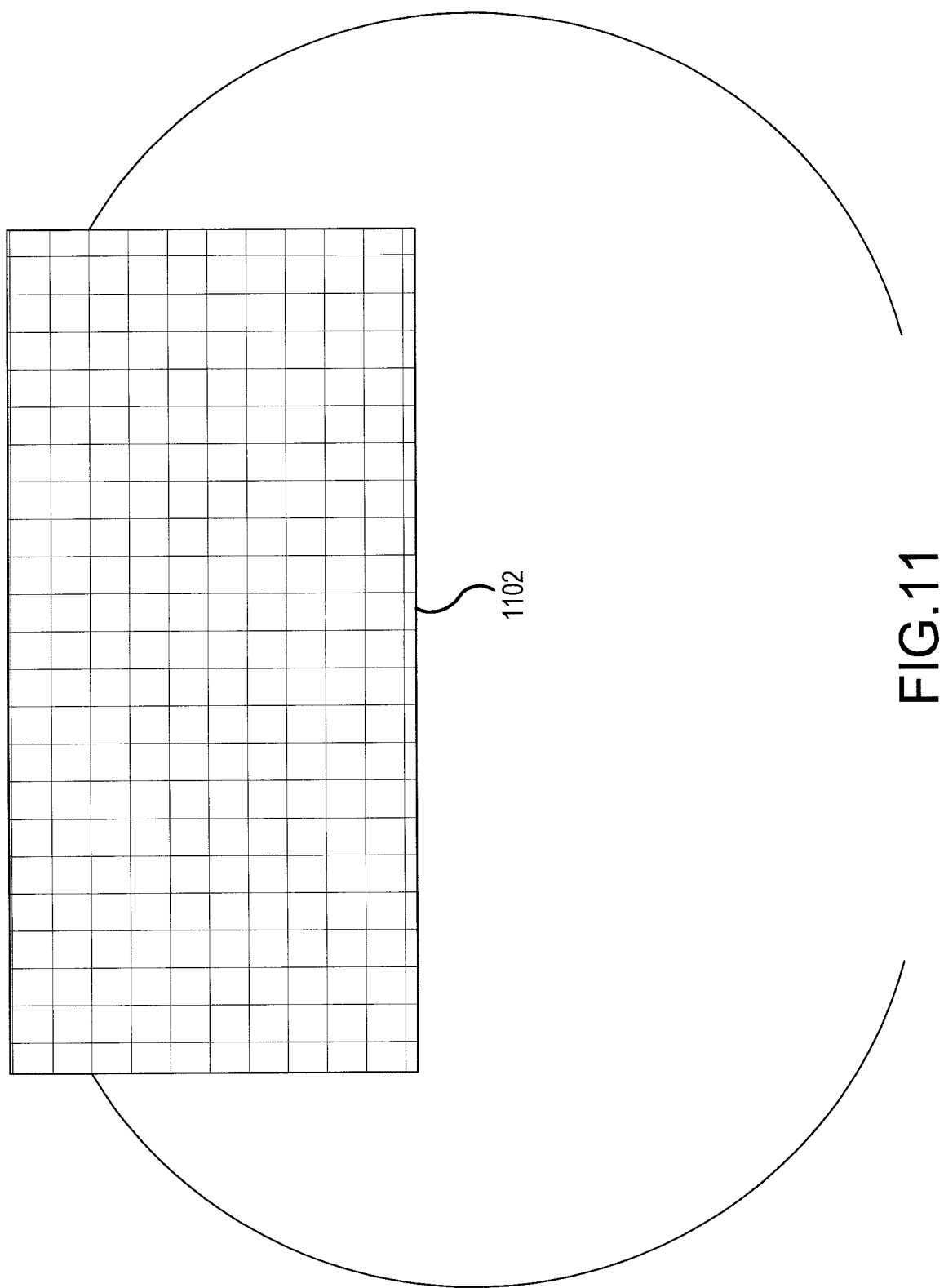
FIG. 11 illustrates another alternative embodiment of an anchor of the cervical retraction system 100.

The suture delivery system can also be used in such a way to create an anchor by stitching in a cross-hatch as shown in FIGS. 10 and 11. That is, the individual anchor (e.g., 110/202) can be created by knitting, using the first end of the suture thread to produce a ball-shaped anchor. The suture anchor is then a respective braided part 1002. In the alternative embodiment illustrated in FIG. 11, a quadrangular, plate-shaped anchor 1102 can be knitted. Thus, the shape of the anchor 1102 is knitted in the middle of a given length of a suture thread to knit the plate-shaped anchor 1102 (i.e., the plate-shaped anchor 202 in the embodiment illustrated in FIG. 4). The knitted anchors 1002/1102 can be used in place of the anchors 110/202 described above.

Thus, the present cervical retraction systems 100/200, in accordance with certain exemplary embodiments of the invention, provide a simple and economical device for retracting cervical tissue during a surgical procedure. Indeed, the structure described above can be used without any additional components. In other words, the cervical retraction system 100 or the cervical retraction system 200 may be formed only of the anchor, the suture(s) and the needle(s) as described above.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A cervical retraction system, comprising:
   a suture having a first end and a second end;
   a cervical anchor secured to the first end of the suture;
   a curved needle secured to the second end of the suture; and
   a thread holder configured to exert a pull on the suture, the thread holder comprising a spool or a fastening pin configured to wind the suture,
   wherein the cervical anchor is elongated along an axis, such that the cervical anchor has a first end and a second end,
   wherein the first end of the cervical anchor is secured to the first end of the suture, such that the first end of the suture is coaxial with the first end of the cervical anchor,
   wherein the cervical anchor is a quadrangular, plate-shaped anchor, having four angles,
   wherein the first end of the cervical anchor tapers towards the first end of the suture, and
   wherein an entirety of the cervical anchor is made of stainless steel, titanium, a titanium alloy or carbon.

2. The system according to claim 1, wherein the suture comprises a resilient strap.

3. The system according to claim 1, wherein the cervical anchor is rigid and is bent with respect to its longitudinal axis.

4. The system according to claim 1, wherein the cervical anchor comprises a slit configured to receive the suture.

5. The system according to claim 1, wherein the entirety of the cervical anchor is made of stainless steel.

6. The system according to claim 1, wherein the thread holder further comprises a main body forming a hand grip.

7. The system according to claim 6, wherein the thread holder further comprises a needle receiving slot formed on the main body.

8. The system according to claim 6, wherein the spool or the fastening pin is disposed at a distal end of the main body.

9. The system according to claim 1, wherein an outer periphery of the cervical anchor is quadrangular.

10. A method of retracting a cervix, comprising:
    providing the cervical retraction system according to claim 1,
    inserting the curved needle through tissue of a cervix of a patient;
    advancing the curved needle along a trajectory of a curve of the curved needle until it emerges through an external os of the cervix; and
    applying counter tension by pulling the curved needle out through the external os using the thread holder, the thread holder configured to wind the suture.

11. A cervical retraction system, comprising:
    a cervical anchor having a first end and a second end;
    a first suture having a first end and a second end, the first end of the first suture secured to and extending from the first end of the cervical anchor;

a second suture having a first end and a second end, the first end of the second suture secured to and extending from the second end of the cervical anchor;
a first curved needle secured to the second end of the first suture;
a second curved needle secured to the second end of the second suture; and
a thread holder configured to exert a pull on the first suture or the second suture, the thread holder comprising a spool or a fastening pin configured to wind the suture,
wherein the cervical anchor is rigid and is bent with respect to its longitudinal axis,
wherein the cervical anchor is a quadrangular, plate-shaped anchor, having four angles,
wherein the first end of the cervical anchor tapers towards the first end of the first suture and the second end of the cervical anchor tapers towards the first end of the second suture, and
wherein an entirety of the cervical anchor is made of stainless steel, titanium, a titanium alloy or carbon.

12. The system according to claim 11, wherein the first suture and the second suture each comprise a resilient strap.

13. A cervical retraction system, comprising:
a suture having a first end and a second end;
a cervical anchor secured to the first end of the suture;
a curved needle secured to the second end of the suture; and
a thread holder configured to exert a pull on the suture,
wherein the cervical anchor is elongated along an axis, such that the cervical anchor has a first end and a second end,
wherein the first end of the cervical anchor is secured to the first end of the suture, such that the first end of the suture is coaxial with the first end of the cervical anchor,
wherein the cervical anchor is a quadrangular, plate-shaped anchor, having four angles,
wherein the first end of the cervical anchor tapers towards the first end of the suture
wherein an entirety of the cervical anchor is made of stainless steel, titanium, a titanium alloy or carbon,
wherein the thread holder comprises:
a main body forming a hand grip; and
a suture winding member disposed on the main body, and
wherein the suture winding member comprises a spool or fastening pin configured to receive the suture.

14. A cervical retraction system, comprising:
a suture having a first end and a second end;
a cervical anchor secured to the first end of the suture;
a curved needle secured to the second end of the suture; and
a thread holder configured to exert a pull on the suture,
wherein the cervical anchor is elongated along an axis, such that the cervical anchor has a first end and a second end,
wherein the first end of the cervical anchor is secured to the first end of the suture, such that the first end of the suture is coaxial with the first end of the cervical anchor,
wherein the cervical anchor is a quadrangular, plate-shaped anchor, having four angles,
wherein the first end of the cervical anchor tapers towards the first end of the suture,
wherein an entirety of the cervical anchor is made of stainless steel, titanium, a titanium alloy or carbon, and
wherein the thread holder comprises:
a cylindrical main body forming a hand grip;
a suture winding member disposed at a distal end of the main body, the suture winding member comprising a spool or fastening pin configured to receive the suture; and
a needle receiving slot formed on a top of the main body and configured to receive the curved needle.

15. A cervical retraction system, comprising:
a suture having a first end and a second end;
a cervical anchor secured to the first end of the suture;
a curved needle secured to the second end of the suture; and
a thread holder configured to exert a pull on the suture, the thread holder comprising:
a cylindrical main body forming a hand grip;
a suture winding member disposed at a distal end of the main body, the suture winding member comprising a spool or fastening pin configured to receive the suture; and
a needle receiving slot formed on a top of the main body and configured to receive the curved needle.

* * * * *